US006839140B1

(12) United States Patent
O'Keefe et al.

(10) Patent No.: US 6,839,140 B1
(45) Date of Patent: Jan. 4, 2005

(54) CAVITY-ENHANCED LIQUID ABSORPTION SPECTROSCOPY

(75) Inventors: Anthony O'Keefe, Cupertino, CA (US); Manish Gupta, Mt. View, CA (US)

(73) Assignee: Los Gatos Research, Mountain View, CA (US)

( * ) Notice: Subject to any disclaimer, the term of this patent is extended or adjusted under 35 U.S.C. 154(b) by 355 days.

(21) Appl. No.: 10/188,541

(22) Filed: Jul. 3, 2002

(51) Int. Cl.[7] ............................................. G01N 21/00
(52) U.S. Cl. ....................................................... 356/436
(58) Field of Search ................................. 356/432–436

(56) References Cited

U.S. PATENT DOCUMENTS

| | | | |
|---|---|---|---|
| 4,303,343 A | 12/1981 | Patel et al. ................. | 356/432 |
| 4,544,274 A | 10/1985 | Cremers et al. ............ | 356/436 |
| 5,444,807 A | 8/1995 | Liu ............................. | 385/125 |
| 5,528,040 A * | 6/1996 | Lehmann ..................... | 250/343 |
| 5,570,447 A | 10/1996 | Liu ............................. | 385/125 |
| 5,604,587 A | 2/1997 | Che et al. .................... | 356/246 |

FOREIGN PATENT DOCUMENTS

EP 1195582 A1 4/2002

OTHER PUBLICATIONS

A. O'Keefe et al., "Cavity Ring–Down Optical Spectrometer for Absorption Measurements Using Pulsed Laser Sources", Rev. Sci. Instrum., vol. 59, No. 12, Dec. 1988, pp. 2544–2551.

A.J. Hallock et al., "Direct Monitoring of Absorption in Solution by Cavity Ring–Down Spectroscopy", Analytical Chemistry, vol. 74, 2002, pp. 1741–1743.

S. Xu et al., "Cavity Ring–Down Spectroscopy in the Liquid Phase", Review Scientific Instruments, vol. 73, No. 2, Feb. 2002, pp. 255–258.

A. O'Keefe et al., "CW Integrated Cavity Output Spectroscopy", Chemical Physics Letters, vol. 307, 1999, pp. 343–349.

World Precision Instruments printout, "Liquid Waveguide Capillary Cell", 2 pages.

Dupont printout, Teflon Amorphous Fluoropolymer, "Unique Properties of Teflon®", 3 pages.

* cited by examiner

*Primary Examiner*—Gregory J. Toatley, Jr.
*Assistant Examiner*—Amanda Merlino
(74) *Attorney, Agent, or Firm*—Schneck & Schneck; Thomas Schneck; Mark Protsik

(57) ABSTRACT

An integrated-cavity output spectroscopy (ICOS) instrument adapted for measuring liquid samples has a low-scatter flow cell arrangement passing through a stable optical cavity defined by an arrangement of two or more mirrors. The flow cell provides a sample volume within the cavity of at most one microliter at any given time. The optical cavity has an effective cavity length of at most one centimeter and mirror radii of curvature for the stable cavity arrangement are much longer than the cavity length. A light beam with stable characteristics is introduced into the cavity, passes through the liquid sample cell multiple times, and a detector measures a portion of the light from the cavity. The light measurement is analyzed to determine absorption by the liquid sample, and related information.

30 Claims, 2 Drawing Sheets

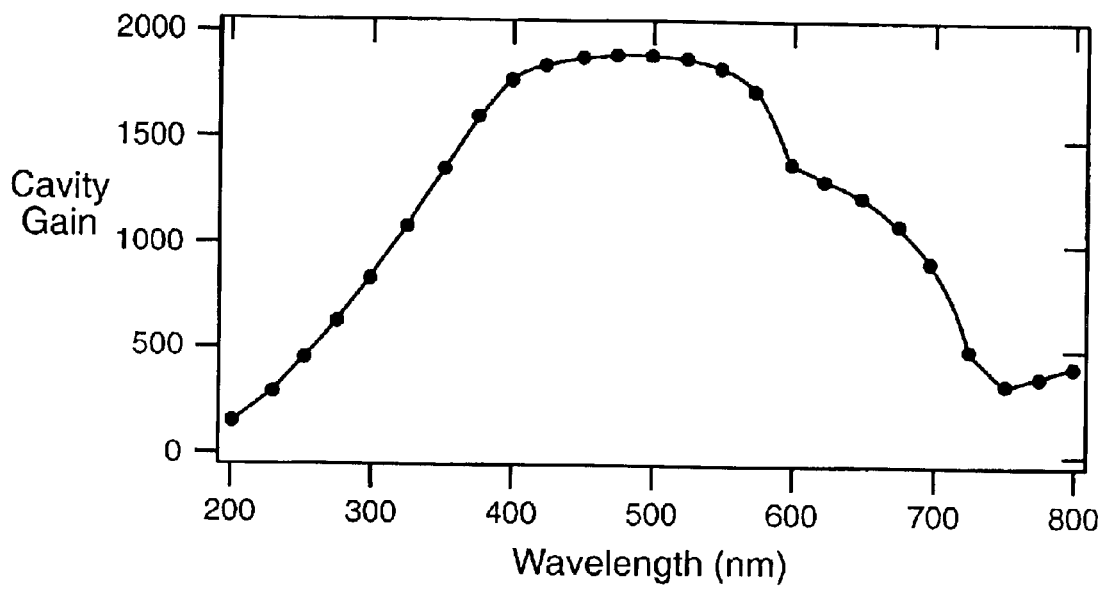
FIG._1
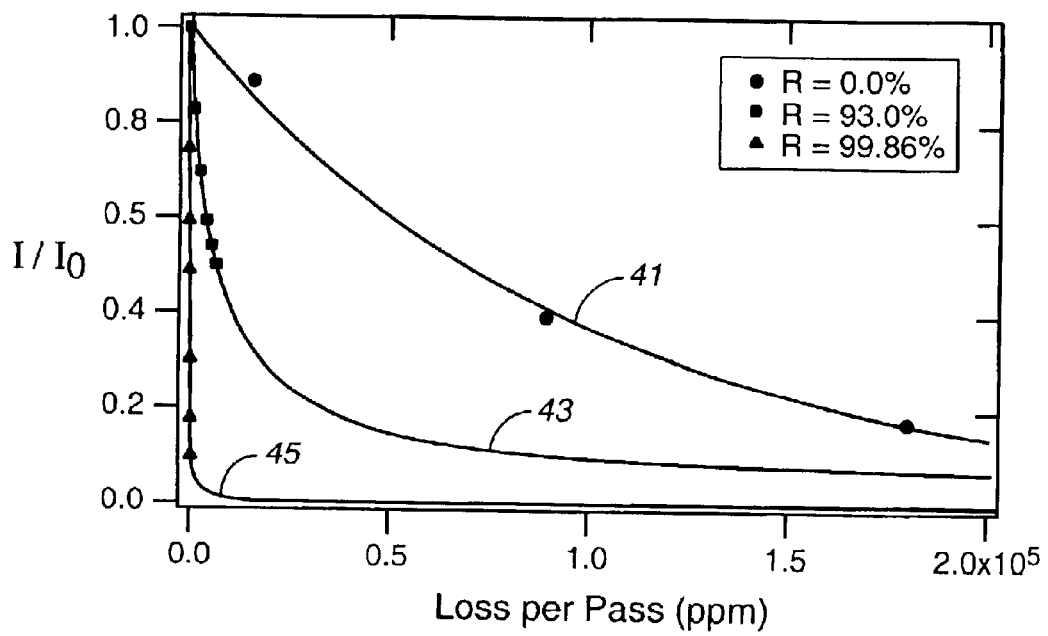
FIG._4

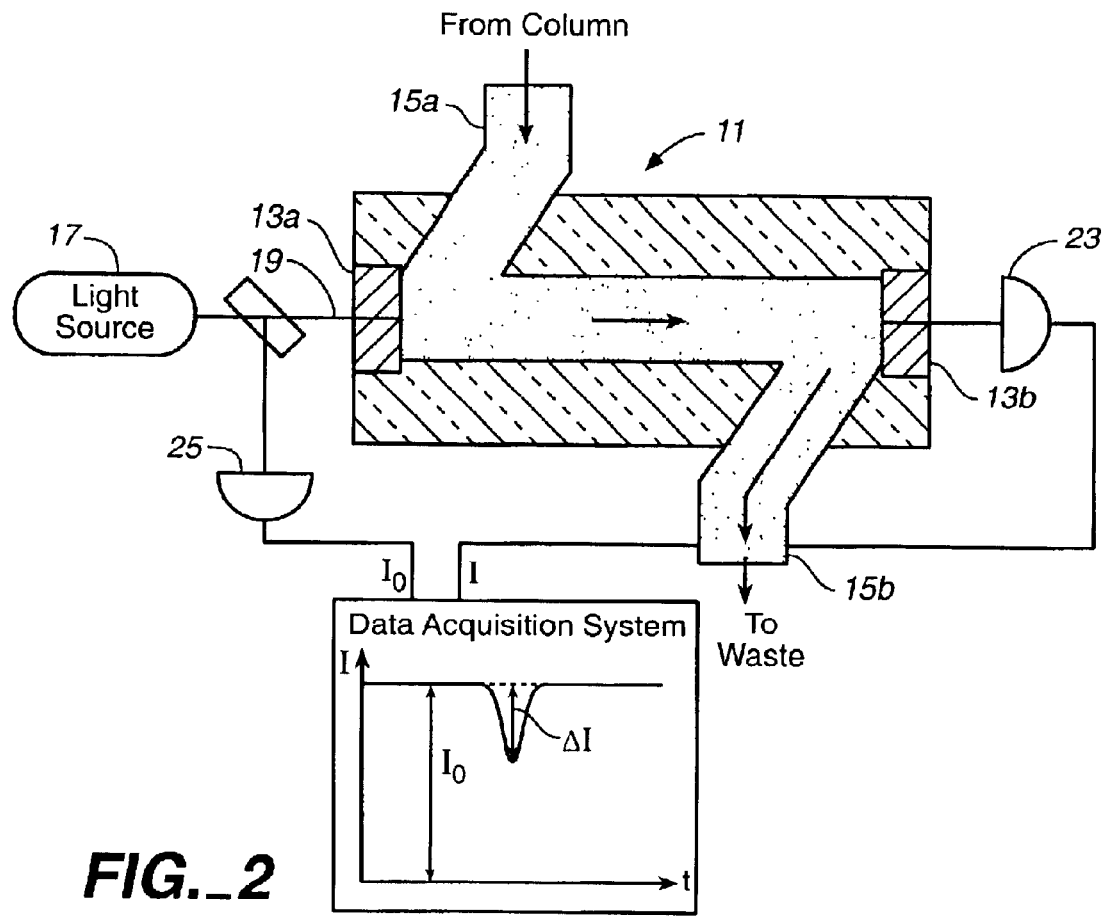
FIG._2
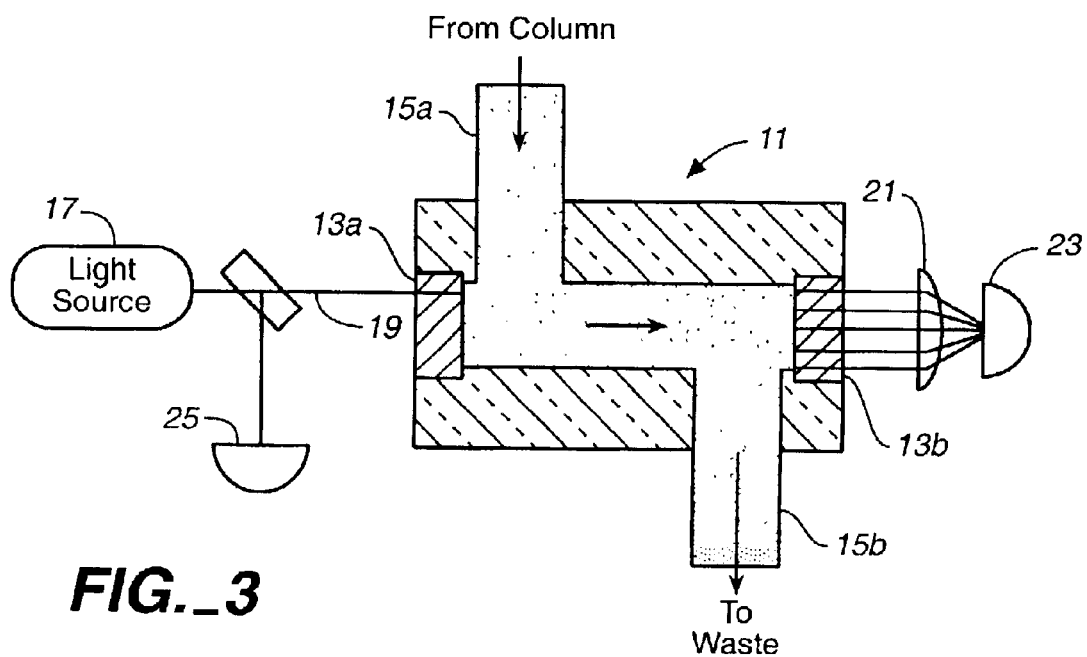
FIG._3

CAVITY-ENHANCED LIQUID ABSORPTION SPECTROSCOPY

TECHNICAL FIELD

The present invention relates to absorption spectroscopy methods and apparatus for chemical analysis, especially such methods and apparatus that employ cavity ring-down spectroscopy (CRDS) and integrated cavity output spectroscopy (ICOS) techniques to increase detection sensitivity. The present invention also relates to absorption spectroscopy methods and apparatus that are adapted for use with liquid samples.

BACKGROUND ART

Conventional absorption spectroscopy is widely applied to probe constituents in the liquid phase. In conjunction with several separation techniques, including High-Performance Liquid Chromatography (HPLC) and Capillary Electrophoresis (CE), absorption spectroscopy has become an indispensable tool in virtually all fields of chemistry. It has been used to provide quantitative determination of many important chemical compounds including species as varied as nucleic acids, amino acids, proteins, carbohydrates, terpenoids, steroids, antibiotics, pharmaceuticals, pesticides, hydrocarbons, and a host of inorganic substances. Most of these analyses have involved using a HPLC or CE column to separate the species and then an absorption detector to measure the species' concentration as they elute off the column. The vast majority of research has involved developing specialized columns for various applications.

There has been some progress in increasing the sensitivity of these absorption detectors, which has mostly focused on using other analytical techniques to measure concentration. These techniques, including fluorescence, electrochemical detection, and mass spectrometry, have increased the sensitivity of HPLC and CE by about a factor of 100–1000. However, these advances have also limited the number of applications and increased complexity. For example, fluorescence detection requires that the molecules of interest be "tagged" with an appropriate dye, electrochemical detection requires that the analyte undergo a redox reaction, and mass spectrometry requires extensive equipment and specialized couplings between the column and the detector. Due to these complexities, absorption is still the most commonly used HPLC and CE detection method. Likewise standard techniques like colorimetry rely on using absorption spectroscopy to detect pH, metal contamination in wastewater, and many titration products.

In conventional absorption spectroscopy, a light source is passed through an absorbing sample. The intensity of the light is measured before, $I_0$, and after, $I$, the absorbing media. The concentration of the absorbing species can be determined from Beer's Law:

$$I/I_0 = e^{-L\sigma c} \propto 1 - L\sigma c$$

where L is the sample length, $\sigma$ is the molecule's absorption cross section, and c is the species' concentration. The minimum detectable concentration of the absorbing species depends on how accurately one can measure the change in light intensity ($\Delta I = I - I_0$). For typical absorption experiments, $\Delta I/I_0 \sim 10^{-4}$ after one second of averaging. Absorption spectroscopy is an attractive analytical tool because it is inexpensive, simple, and provides an absolute concentration without calibration. Unfortunately, conventional absorption spectroscopy does not provide the sensitivity necessary for many analytical applications.

The sensitivity of absorption spectroscopy can be increased by either measuring $\Delta I$ more accurately or by use of a longer sample path length. The latter can be simulated by passing the light through the liquid cell several times (multi-pass cell) to increase the path length by an order of magnitude. One of the most common methods employed to measure $\Delta I$ more accurately in liquids is photoacoustic spectroscopy (U.S. Pat. No. 4,303,343), which relies on measuring the acoustic wave generated by absorption in liquids. Although this technique can be very sensitive due to its background-free detection method, it requires very high-power lasers (1 Watt) to achieve the sorts of sensitivities described in this patent and is therefore not widely applicable. Another proposed technique utilizes thermal-lensing effects in liquid samples to measure weak absorptions (U.S. Pat. No. 4,544,274) by placing the liquid cell within a laser cavity. This method is also limited in utility due to its complexity and specialized equipment.

World Precision Instruments supplies a commercial absorption spectroscopy instrument based on a liquid waveguide capillary cell (cf., U.S. Pat. Nos. 5,444,807; 5,570,447; and 5,604,587). The instrument uses a 1 to 10 meter long, hollow capillary tube made of (or coated with) Teflon AF. The tube is filled with liquid and light is coupled into the capillary. Similar to an optical fiber, the light is confined within and propagates down the length of the tube. The net absorption is measured by comparing the light intensity before and after the capillary. An advantage of this technology is that a small sample volume (200 microliters per meter of tubing) can extend over a very long light path. The system can use very robust, inexpensive parts, e.g., LEDs or lamps for the light source. However, for some analytical separation techniques, including HPLC and CE, the resolution (ability to distinguish separated compounds) is directly dependent on the volume of the analyzer and the capillary length, and thus much smaller liquid volumes than those used in this instrument are needed.

In 1988, Anthony O'Keefe and David A. G. Deacon introduced the idea of Cavity Ring Down Spectroscopy (CRDS). ("Cavity Ring-Down Optical Spectrometer for Absorption Measurements Using Pulsed Laser Sources", Review of Scientific Instruments, vol. 59, no. 12, December 1988, pp. 2544–2551) In CRDS, light passes through the mirror in order to enter the cavity and is detected by passing through the output mirror. Unlike multi-pass methods, there is not an entrance or exit hole in either mirror. If the light is of the correct frequency, it constructively interferes with itself and builds up in the optical cavity. When the intensity has built up sufficiently, the laser is rapidly blocked and the decay of light intensity out of the cavity is measured. If the system is well aligned, this decay will be exponential with a time constant, $\tau$, which depends on all of the losses in the cavity. These losses include mirror transmission (typically on the order of 100 ppm) and any absorption or scatter in the cavity. The major advantage of CRDS is that the effective path length of the absorbing species is dependent on the reflectivity of the mirrors, $L_{eff} = L/(1-R)$. In a one-meter long gas cell with highly reflective mirrors (R~99.99%) the effective path length approaches 10,000 meters. This enormous enhancement in effective path length allows for very small concentrations to give rise to detectable changes in $\tau$. Moreover, since $\tau$ is an absolute measure of cavity loss, CRDS gives an absolute concentration without need for calibration. Due to these advantages, CRDS has since led to over 300 publications worldwide, and is emerging as a powerful new analytical tool.

Unfortunately, CRDS cannot be applied effectively to liquids. The large scattering losses in liquids coupled with short cavity lengths result in a very short ringdown time that is difficult to accurately measure. Most liquid cells, especially those used in HPLC and CE, have path lengths on the order of 1–10 mm. Even with high reflectivity mirrors, the ringdown time of these cells is less than 100 nanoseconds, which is too fast to measure very accurately.

Despite these limitations, a research group at Stanford University has recently demonstrated cavity ringdown spectroscopy in a liquid cell. (A. J. Hallock, et al., "Direct Monitoring of Absorption in Solution by Cavity Ring-Down Spectroscopy", Analytical Chemistry, vol. 74, pp. 1741–1743 (2002)) In their system, a long (~21 cm) liquid cell is bounded by two high-reflectivity mirrors. Pulsed laser light is injected through one of the mirrors and a photomultiplier tube is used to measure the transmitted intensity through the other mirror. The residence time of the light in the cavity is determined by the total loss in the system that is given by the sum of the mirror transmission and losses due to scatter and absorption in the media. Typically, these ringdown times are on the order of 400 ns and require a pulsed dye laser coupled with a fast detector and data acquisition system. The main limitation in this design is the very large liquid cell required to gain measurable cavity ringdown times (minimum volume of 5 mL). As noted above, many of the key applications of enhanced liquid absorption spectroscopy require very small sample volumes (microliters) and are therefore not amenable to this system.

A similar CRDS system for liquid samples is described in a paper by S. Xu, et al., "Cavity ring-down spectroscopy in the liquid phase", Review of Scientific Instruments, vol. 73, pp. 255–258 (2002). In that system, a short (1 cm) liquid cell is inserted into a much longer (48 cm) optical cavity. Like all of these cavity-based systems, they pass the light multiple times through the cell containing the liquid sample, thus multiplying the 1 cm path length through the cell to an effective 900 cm length. By super-polishing the walls of the liquid cell and placing them at precisely Brewster's angle (the cell is very alignment sensitive), they can minimize scattering losses from the cell walls. In addition to requiring a specialized highly polished glass cell that is precisely placed, the cavity itself is also alignment sensitive. Any misalignment of the cavity mirrors not only decreases the accuracy of the analysis, but also changes the way the beam passes through the liquid cell, introducing additional loss. Also, if a different liquid solvent is used, with a different refractive index, the liquid cell must also be changed (cut at a different angle) in order to prevent introducing scattering loss.

Integrated Cavity Output Spectroscopy (ICOS) was developed at Los Gatos Research, Inc., Mountain View Calif., to enhance the sensitivity of absorption spectroscopy for use with very small sample volumes. (A. O'Keefe, J. J. Scherer, and J. B. Paul, "CW Integrated Cavity Output Spectroscopy", Chemical Physics Letters, vol. 307, no. 5–6, Jul. 9, 1999, pp. 343–349). This technique is similar to CRDS in that it uses a high-finesse optical cavity, but does not involve blocking the laser or measuring cavity decay. Instead, the intensity of the beam passing through the cavity is continuously measured similar to a standard absorption experiment. The measured output varies randomly between high intensity and no intensity as the laser wanders slowly in and out of resonance with the cavity (due to mechanical and thermal drifts). In order to randomize this transmission on a faster timescale (and thus allow for faster signal averaging), the laser is dithered while the cavity length is slightly oscillated using a piezoelectric transducer. This forced fast randomization allows the cavity output to be averaged to within $\Delta I/I_0 \sim 10^{-2}$ in one second. Although this is significantly noisier than standard absorption, ICOS retains the long effective path length realized in CRDS. In order to calibrate ICOS, it is necessary to know the reflectivities of the mirrors, which can be determined using CRDS prior to installment or by measuring an absorption standard. Until now, ICOS has only been used with gas samples.

In 2000, Joshua Paul and Anthony O'Keefe developed Off-Axis ICOS (see assignee's pending U.S. patent application Ser. No. 09/976,549, filed Oct. 12, 2001, and incorporated by reference herein), a more sensitive variant of ICOS that does not rely on high-voltage components. The sensitivity of ICOS is limited by the large variations in output intensity due to the light constructively and destructively interfering with itself in the cavity. In order to decrease $\Delta I/I_0$, it is necessary to quell these interferences. In ICOS, these interferences were partially suppressed by dithering both the cavity and the laser. In Off-Axis ICOS, these interferences are almost completely eliminated by aligning the cavity in an off-axis configuration. This configuration, coupled with the slight astigmatism of the cavity mirrors, increases the beam's reentrant condition from a single pass (for standard ICOS) to almost 1000 passes. For most laser light sources, after the 1000 passes, the light is unable to interfere with itself because the distance it has traveled exceeds the coherence length of the laser. Thus, the cavity output is much more stable than standard ICOS and $\Delta I/I_0 \sim 10^{-4}$ can easily be achieved with only one second of averaging without the use of any high-voltage transducers. Moreover, since the off-axis beam path is not unique, the system is extremely insensitive to changes in alignment, making it much more robust than multi-pass cells, CRDS, or ICOS. The effective path length of Off-Axis ICOS is again related to the reflectivity of the mirrors and is typically ~10000 times the cavity length.

An object of the present invention is to provide a cavity-based absorption spectroscopy apparatus adapted to measure liquid samples of small volume (~microliters) with enhanced absorption sensitivity.

DISCLOSURE OF THE INVENTION

The present invention applies the ICOS technique to small volume liquid samples in an apparatus that utilizes continuous-wave (cw) or pulsed light sources coupled into a short high-finesse optical cavity to enhance the absorption sensitivity in liquids. We have discovered that, unlike CRDS, ICOS can be employed with liquid cells of very small volume. Since the cavity loss is determined by the continuous cavity throughput and does not require ringdown, the liquid cell can have very short path lengths. In this case, the ICOS cavity makes a small sample length (~1 mm) act like a much longer length (~10 meters). Typical cavity lengths are a few millimeters or less, with typical sample volumes (in the cavity) being a few microliters or less. The light transmitted through the cavity is continuously measured and the cavity enhancement is determined either from the mirror reflectivities or by use of standard absorption references.

The invention can be implemented with either an incoherent or a coherent light source, including broad spectrum and multimode sources. In the case of coherent light sources, off-axis injection may be used to avoid interferences in the optical cavity. Likewise, dithering the laser frequency and/or cavity length may also be used to suppress these interferences with either axial or off-axis injection.

The present invention enhances the sensitivity of standard absorption methods by a factor of 700, or 1000 or more, making it one of the most sensitive liquid absorption detection schemes. Due to countless applications of absorption, this enhanced detection will allow for unheralded advancements in analytical sciences.

BRIEF DESCRIPTION OF THE DRAWINGS

FIG. 1 is graph of the cavity gain versus wavelength of a 1 mm liquid (water) cell bounded by two mirrors of 99.95% reflectance (500 ppm of loss).

FIGS. 2 and 3 are schematic plan views of two embodiments of cavity-enhanced liquid absorption spectrometers in accord with the present invention. FIG. 2 shows a preferred on-axis embodiment, while FIG. 3 shows an alternative off-axis embodiment.

FIG. 4 is a graph of output v. input intensity ratio $I/I_0$ versus per-pass loss in the optical cavity for three different cavity mirror reflectances R, showing how ICOS optical cavities like those in FIGS. 2 and 3 enhance absorption sensitivity in liquids. The points represent measured values and the solid lines are the predicted transmission. The measurements were made using an off-axis ICOS instrument like that in FIG. 3.

BEST MODE OF CARRYING OUT THE INVENTION

The basic concept of cavity-enhanced absorption has been well studied and documented. A high-finesse optical cavity is arranged in a stable configuration such that the radii of curvature of the mirrors, $R_1$ and $R_2$, and the distance between the mirrors, d, satisfy the inequality $$0 < \left(1 - \frac{d}{R_1}\right)\left(1 - \frac{d}{R_1}\right) < 1$$

Light from either a coherent or incoherent source is injected through the first mirror and detected beyond the second mirror. The absorbing sample (in the present invention, a liquid) is contained between the mirrors and transmission through the optical cavity is measured. If a coherent light source is implemented, either off-axis injection or a dithering of the laser and cavity frequencies can be used to avoid interferences inside the cavity. In the absence of such interferences, the intensity transmitted through the second cavity mirror, $I_T$, is given by $$I_T = \frac{I_L C_P T^2}{2(1 - R + L + A)}$$

where $I_L$ is the laser intensity, $C_p$ is a cavity coupling parameter, T is the average mirror transmission, L is any loss due to absorption and/or scatter in the sample (liquid) media, and A is loss due to absorption by added species. This equation can be rewritten to demonstrate the advantage of using a high-finesse optical cavity by expressing the change in transmitted intensity, $\Delta I$, as $$\frac{\Delta I}{I_T} = \frac{GA}{1 + GA}$$

where $G = R/(1 - R + L)$. For weak absorptions, $GA \ll 1$, and the cavity provides a linear absorption signal gain. Note that the cavity gain depends on both the mirrors' reflectivity and scattering/absorption losses in the liquid media. FIG. 1 shows how the cavity gain varies with wavelength for a 1 mm long water cell bounded by two mirrors of 99.95% reflectivity each. The scattering and absorption losses of water as a function of wavelength, which are used to obtain the gain values in FIG. 1, are derived from measured values listed in the published paper by George M. Hale and Marvin R. Querry, "Optical constants of water in the 200-nm to 200-$\mu$m wavelength region", Applied Optics 12, pp. 555–562 (1973). It can be seen that ICOS greatly enhances liquid absorption sensitivity.

A schematic of the preferred embodiment of the present invention is depicted in FIG. 2. A low-volume liquid cell 11 is formed with two highly reflecting curved mirrors 13a and 13b aligned to produce a high-finesse stable optical cavity. The mirror reflectivities should be higher than 99% for best results, but reflectivities as low as 50% could be used. Preferred mirror reflectivities R are in the range 99%–99.99%. The mirrors are spaced closely apart, with separations being approximately 1 centimeter or less. Typical mirror separations are in the range from 0.1 to 2.0 mm. Mirror radii of curvature are typically 0.1–6.0 meters. Long focal lengths (relative to the mirror separation or cavity length) have been found to be least sensitive to changes in both mirror alignment and spacing, and thus are preferred.

The sample liquid which is flowed through the cell 11 from an inlet 15a to an outlet 15b can come from a variety of sources, including analytical separation columns. The liquid sample volume in the optical cavity is determined in this cell construction by the size of the mirrors and the spacing between them. Typically, the volume will be restricted to about 0.5–100 microliters by employing small mirrors (2–4 mm diameter) spaced closely apart (as specified above). A sample volume of 10 microliters or less is preferred for use with HPLC and CE analytical separation techniques in order to obtain adequate resolution of the separation of compounds in the sample.

A light source 17 provides a collimated light beam 19, which impinges upon the cell 11 through one of the mirrors 13a. In FIG. 2, an axial arrangement, in which the light beam 19 is introduced into the optical cavity along the optical axis of the cavity, is used. The source 17 may be either an incoherent source (e.g., LEDs, lamps, glowbars) or a coherent source (e.g., diode or gas lasers). The short cavity length allows somewhat divergent sources, such as LEDs, to be used. Sources can be broad spectrum and multimode. The wavelength of the light source is limited to the areas in which the liquid sample does not absorb significantly (e.g., 200–800 nm in water) and can be further restricted by optical filtering if a broad band optical source is being used in order to target a specific absorber. If a coherent source is used with the FIG. 2 axial configuration, either the laser wavelength or the cavity length can be dithered using known techniques to minimize interference effects.

Light passing through the cell 11 and exiting through mirror 13b is incident onto an amplifying detector 23 (e.g., a photomultiplier tube or silicon photodiode). A small fraction (about 5%) of the light 19 is split-off onto a reference detector 25 to permit normalization of the signal intensity. A data acquisition system receives the light measurement data from the detectors 23 and 25. The voltage signal from the detector is averaged over some time period (typically one second), normalized to the reference signal, and recorded. If the device is being used to detect species eluting from a separation column, the normalized signal can be recorded as a function of time. The normalized data may be processed to analyze the sample passing through the cell 11.

In the case of coherent light sources, off-axis ICOS may be desired (either in place of or in addition to dithering) to avoid interferences in the optical cavity. An off-axis ICOS embodiment of the invention is shown in FIG. 3. This version is substantially identical to that seen in FIG. 2, except that the light 19 is introduced into the optical cavity along an off-axis light path of the cavity. Successive reflections at any given mirror occur at different locations on the mirror. A lens 21 is used to focus light exiting through mirror 13b onto the detector 23.

A version of this off-axis embodiment was used in our preliminary studies of applying ICOS techniques to small volume liquid samples. That particular system consisted of a 15 mW argon-ion laser source 17 providing a beam 19 (single line, 488 nm) impingent on a liquid cell 11 in an off-axis configuration. The liquid cell 11 was 1 cm long and bound by two mirrors 13a and 13b. Light exiting the cell was collected by a lens 21 and focused onto a photomultiplier tube (PMT) 23. Water was pumped through the cell 11 using a dye-circulating pump. This apparatus was used to test the principles of liquid ICOS by preparing a stock solution consisting of a diluted water-soluble blue dye.

FIG. 4 shows the test results obtained using this apparatus. The sample cell 11 was first equipped with windows (instead of mirrors 13a and 13b) and the stock solution was circulated through the system. The change in transmitted intensity between pure water and the stock solution was measured. Several controlled dilutions of this stock solution were then introduced into the system and similar measurements were made. Using these measurements, a calibration curve was derived and the loss per pass, S, was determined to be $S=1-e^{-1.8}c$, where c is the fraction of stock solution in the measured sample. This produces the curve 41 for R=0%. The windows in the cell 11 were then replaced with mirrors 13a and 13b. For the first test, the two mirrors had an average reflectivity of <R>=93%. Transmission was measured for several dilutions of the stock solutions, and cavity-enhanced absorption was observed. The data matched the theoretically predicted transmission using the average <R>= 93% (curve 43) and showed an sensitivity enhancement factor of ~14. A second test was conducted using a different set of mirrors in hopes of further enhancing the absorption sensitivity. This experiment utilized mirrors with $R_1=R_2=$ 99.86% (as determined by CRDS). Similar measurements were taken, which matched the predicted transmission (curve 45). This cavity showed an enhancement of ~700. The experimental evidence indicates that liquid ICOS provides the expected enhancement in absorption sensitivity.

What is claimed is:

1. An integrated-cavity output spectroscopy (ICOS) instrument, comprising:

an arrangement of two or more mirrors forming an optical cavity, the cavity adapted to receive an absorption cell with a sample to be tested, the optical cavity having an effective cavity length of at most one centimeter, the absorption cell providing at most one micro-liter sample volume at any given time within the optical cavity;

a continuous-output light source providing a light beam with stable characteristics which is introduced into the optical cavity;

a detector situated in a position to receive and measure a portion of the light beam from the optical cavity; and means for processing data representing the light measurement from the detector for analyzing a sample received by the optical cavity.

2. The instrument of claim 1 wherein the sample received by the optical cavity is a liquid sample.

3. The instrument of claim 1 wherein the absorption cell providing the sample to the optical cavity comprises a low-scatter flow cell arrangement passing through the optical cavity.

4. The instrument of claim 1 wherein at least one of the mirrors has a curved reflecting surface, and the two or more mirrors are arranged to form a stable optical cavity.

5. The instrument of claim 1 wherein each of the mirrors has a reflectivity of at least 50% at the detected wavelengths.

6. The instrument of claim 5 wherein each of the mirrors has a reflectivity of at least 99 percent such that the optical cavity has high finesse (Q).

7. The instrument of claim 1 wherein the light source is a broad-spectrum incoherent source.

8. The instrument of claim 7 wherein the light source is a light emitting diode (LED).

9. The instrument of claim 1 wherein the light source is a continuous-wave (cw) laser.

10. The instrument of claim 9 wherein the wavelength of the laser is dithered.

11. The instrument of claim 1 wherein the light beam is introduced into the optical cavity along an axial light path of the optical cavity.

12. The instrument of claim 11 wherein the cavity length is dithered.

13. The instrument of claim 1 wherein the light beam is introduced into the optical cavity along an off-axis light path of the cavity, wherein successive reflections at any given mirror occur at different locations thereon.

14. The instrument of claim 1 wherein the detector is positioned to receive light exiting the optical cavity through one of the mirrors thereof.

15. The instrument of claim 1 further comprising a reference detector positioned to receive a portion of light output by the light source.

16. The instrument of claim 15 wherein the means for processing data performs a normalizing of the data using the reference detector.

17. An integrated-cavity output spectroscopy (ICOS) instrument for measuring liquid samples, comprising:

an arrangement of two or more curved mirrors forming a stable optical cavity, the optical cavity having an effective cavity length of at most one centimeter with mirror radii of curvature being much longer than the cavity length;

a low-scatter flow cell arrangement passing through the cavity, the flow cell adapted to receive a liquid sample to be tested, the flow cell providing at most one micro-liter sample volume at any given time within the optical cavity;

a continuous-output light source providing a light beam with stable characteristics which is introduced into the optical cavity;

a detector situated in a position to receive and measure a portion of the light beam from the optical cavity; and means for processing data representing the light measurement from the detector for analyzing said liquid sample received by the optical cavity.

18. The instrument of claim 17 wherein the cavity mirrors are disposed on opposite sides of the flow cell.

19. The instrument of claim 17 wherein the cavity mirrors have a reflectivity of at least 50%.

20. The instrument of claim 19 wherein the cavity mirrors have a reflectivity of at least 99%.

21. The instrument of claim 17 wherein the light source is a broad-spectrum incoherent source.

22. The instrument of claim 21 wherein the light source is a light emitting diode (LED).

23. The instrument of claim 17 wherein the light source is a continuous-wave (cw) laser.

24. The instrument of claim 23 wherein the laser wavelength is dithered.

25. The instrument of claim 17 wherein the light beam is introduced into the optical cavity along an axial light path of the optical cavity.

26. The instrument of claim 25 wherein the cavity length is dithered.

27. The instrument of claim 17 wherein the light beam is introduced into the optical cavity along an off-axis light path of the cavity, wherein successive reflections at any given mirror occur at different locations thereon.

28. The instrument of claim 17 wherein the detector is positioned to receive light exiting the optical cavity through one of the mirrors thereof.

29. The instrument of claim 17 further comprising a reference detector positioned to receive a portion of light output by the light source.

30. The instrument of claim 29 wherein the means for processing data performs a normalizing of the data using the reference detector.

* * * * *

UNITED STATES PATENT AND TRADEMARK OFFICE
CERTIFICATE OF CORRECTION

| | |
|---|---|
| PATENT NO. | : 6,839,140 B1 |
| APPLICATION NO. | : 10/188541 |
| DATED | : January 4, 2005 |
| INVENTOR(S) | : Anthony O'Keefe and Manish Gupta |

It is certified that error appears in the above-identified patent and that said Letters Patent is hereby corrected as shown below:

Column 1, line 57, "$I/I_0 = e^{-L\sigma c}\ \alpha\ 1-L\sigma c$" should read -- $I/I_0 = e^{-L\sigma c} \approx 1-L\sigma c$ --.

Signed and Sealed this

Twenty-fourth Day of March, 2009

JOHN DOLL
*Acting Director of the United States Patent and Trademark Office*